United States Patent [19]

Yen-Hui

[11] Patent Number: 5,005,246

[45] Date of Patent: Apr. 9, 1991

[54] REPLACEABLE TOOTH BRUSH WITH TONGUE SCALER

[76] Inventor: Lin Yen-Hui, No. 6, Lane 55, Tao Yuan Road, Changhua, Taiwan

[21] Appl. No.: 409,610

[22] Filed: Sep. 18, 1989

[51] Int. Cl.⁵ ............................................. A47L 13/12
[52] U.S. Cl. .................................. 15/111; 15/167.1; 15/176.1; 15/176.6; 606/161
[58] Field of Search ................... 15/111, 167.1, 167.2, 15/176.1, 176.4, 176.5, 176.6; 606/161

[56] References Cited

U.S. PATENT DOCUMENTS

| | | | |
|---|---|---|---|
| 1,495,675 | 5/1924 | Colt | 15/111 |
| 1,797,946 | 3/1931 | Eichel | 15/176.1 |
| 1,908,510 | 5/1933 | Dodson | 15/176.4 |
| 1,910,304 | 5/1933 | McKinley | 15/176.6 |
| 1,947,720 | 2/1934 | Laub | 15/176.1 |
| 2,517,029 | 8/1950 | Ridner | 15/176.1 |
| 3,103,680 | 9/1963 | Krichmar | 15/176.4 |

FOREIGN PATENT DOCUMENTS

| | | | |
|---|---|---|---|
| 384303 | 4/1908 | France | 15/176.5 |
| 334346 | 1/1936 | Italy | 15/176.1 |
| 13341 | of 1884 | United Kingdom | 15/111 |

Primary Examiner—Harvey C. Hornsby
Assistant Examiner—Mark Spisich
Attorney, Agent, or Firm—Bacon & Thomas

[57] ABSTRACT

A toothbrush provided with a replaceable bristle holder that is detachably receivable within a trough formed in the brush head and secured in position by a head cover, with the cover and the trough being configured for engaging corresponding portions of the bristle holder. A tongue scaler is slidably supported within the handle portion of the brush and a corresponding handle cover provided with a track engageable by a tenon formed on an end of the scaler to permit the scaler to be extended into a position of use or retracted into a position of storage with respect to the handle.

1 Claim, 2 Drawing Sheets

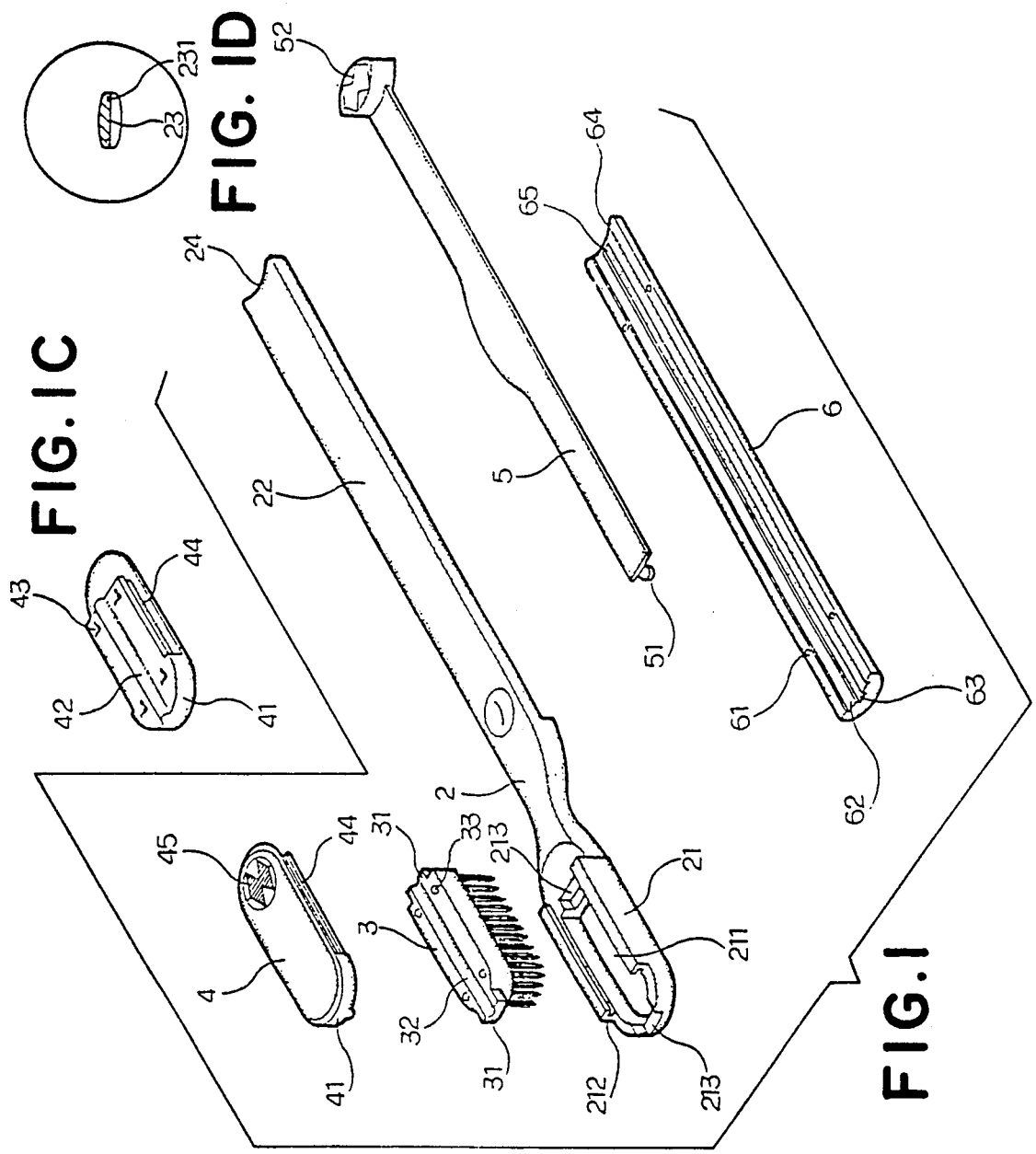

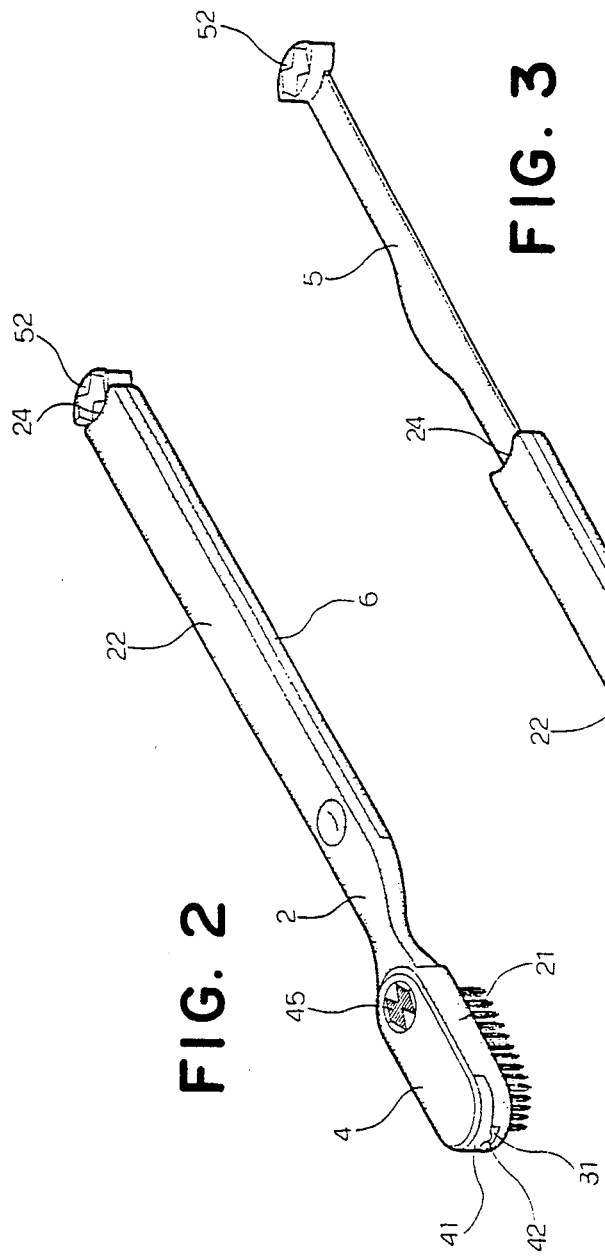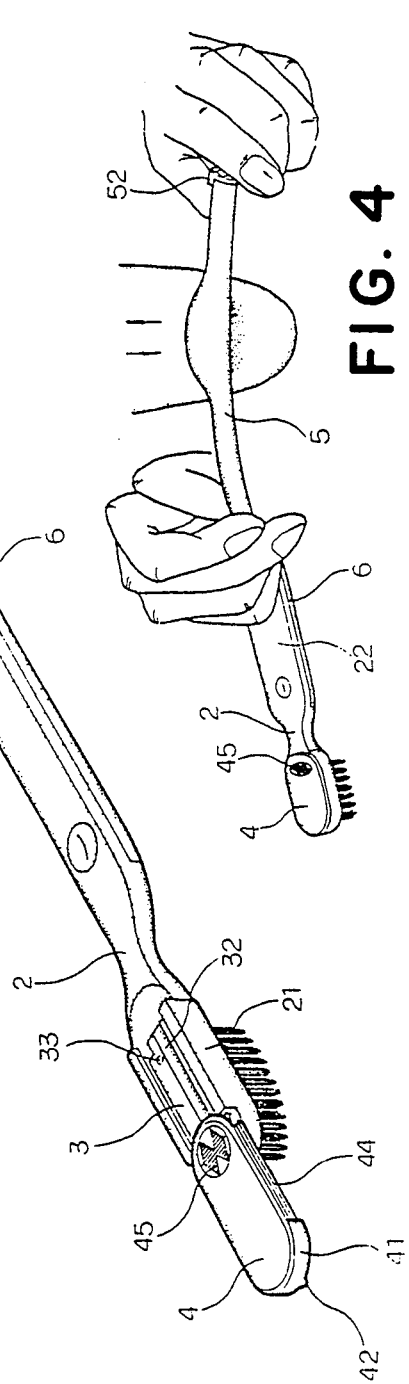

REPLACEABLE TOOTH BRUSH WITH TONGUE SCALER

BACKGROUND OF THE INVENTION

1. Field of the Invention

The present invention relates to a replaceable tooth brush with tongue scaler, which is comprised of a brush handle, a bristle holder, a head cover, a scaler and a handle cover and serves to clean teeth as well as to remove the fur from the human tongue.

2. Description of the Prior Art

Regular tooth brushes are generally comprised of a brush handle with bristles planted on the front end or the head of the brush handle. After a certain period in use, the bristles easily wear away or become slit. If the worn and slit tooth brush is still used, it will be unable to thoroughly clean the teeth and may possibly do injury to the gingiva. Therefore, when a tooth brush is worn out, one normally will dispose of it and buy a new one. However, to throw away a whole tooth brush is not economical. For saving cost, a variety of tooth brushes comprising replaceable brush heads or bristle holders have been produced to solve this problem. There are still problems in these replaceable type tooth brushes, which may include the following:

1. The tooth brushes in which a brush head is connected to a brush handle by means of screw joint tend to become loose because of the resistance force which results during brushing of tooth brush against the teeth and gingiva.
2. The tooth brushes in which a bristle holder is connected to a brush handle by means of a slide-in joint experience loosening of the bristle holder because the tooth brush is used to brush teeth along all directions and the bristle holder is driven to rub against the resistance force imposed by the teeth during the brushing process.

Further, the human tongue is a very sensitive organ comprised of a variety of papillae. During eating, food may reside in the gingival crevice and may also accumulate on the body of the tongue to form into one layer of fur which may produce an odor and impart a dry and bitter feeling.

In order to remove the fur from the tongue, people may directly use a toothbrush or a spoon to scale the tongue. However, a toothbrush can not completely remove the fur from a tongue and a spoon is very inconvenient to utilize in the mouth. Therefore, they are both not very practical in use because they are not specifically designed for such purpose.

In consequence, there is a known tongue scaler which is generally comprised of a flexible spring plate. When in use, the tongue scaler is bent in a curved shape and used to remove the fur from the tongue. Because the human tongue is generally comprised of a variety of papillae, the upper surface of the lingua body is not smooth. Therefore, the fur can only be completely removed from a tongue by repeatedly performing the scaling process.

SUMMARY OF THE INVENTION

The main object of the present invention is to provide a replaceable tooth brush with tongue scaler which includes a brush handle having an integral brush head at the front for setting therein of a bristle holder and for the mounting thereon of a head cover to secure the holder in position. The brush head includes a receiving trough set therein, one pair of inwardly directed guide tracks at both sides, and a notch formed at each of its front and rear ends.

Another object of the present invention is to provide a replaceable tooth brush with tongue scaler which includes a bristle holder replaceably set in the receiving trough of the brush head and comprising two projections set at the front and the rear end thereof for engaging the notches of said brush head, an axial elongated slide way set at the top, and a plurality of positioning dowels disposed on both sides of the slide way.

Another object of the present invention is to provide a replaceable tooth brush with tongue scaler which includes a head cover slidably connected to the brush head and comprising a stopper made at the front, an axial rod-like slide guide formed on the bottom surface, two pairs of positioning recesses symmetrically and oppositely formed at both ends, and stepped tracks formed at both sides.

Another object of the present invention is to provide a replaceable tooth brush which includes a tongue scaler comprising a tenon-like front slide guide and an oval pull end, the scaler being receivable in the brush handle and extendable therefrom for removing fur from the human tongue.

A yet further object of the present invention is to provide a replaceable tooth brush with tongue scaler which further includes a handle cover defining a receiving space with the brush handle for setting therein of the tongue scaler and comprising a plurality of pairs of positioning dowels symmetrically made on the top, an axial groove made on the top to define therein a slide way, a curved rear end, and a stop wall made on the curved rear end.

BRIEF DESCRIPTION OF THE DRAWINGS

The foregoing and other objects, features and advantages of the present invention will be best understood from the following description, the appended claims and the accompanying drawings in which:

FIG. 1 is an exploded perspective view of a tooth brush according to the present invention;

FIG. 1A is a transverse cross-sectional view of the head cover;

FIG. 1B is a transverse cross-sectional view of the brush head;

FIG. 1C is a perspective view depicting the underside of the head cover;

FIG. 1D is a transverse cross-sectional view of the handle portion showing the recess formed therein for receiving the tongue scaler;

FIG. 2 is a perspective view of a fully assembled toothbrush according to the present invention;

FIG. 3 is a perspective view of a partially disassembled toothbrush according to the present invention; and FIG. 4 illustrates the application of the present invention to scale a tongue.

DETAILED DESCRIPTION OF THE PREFERRED EMBODIMENT

Referring to FIGS. 1 and 2, there is shown a replaceable tooth brush with tongue scaler generally comprised of a brush handle 2, a bristle holder 3, a head cover 4, a tongue scaler 5, and a handle cover 6.

The brush handle 2 has a curved rear end 24 and an integral brush head 21 at the front, which brush head 21 includes a receiving trough 211 set therein, one pair of guide tracks 212 formed internally at both sides, and one pair of notches 213 formed respectively at both front and rear ends.

The bristle holder 3 includes two projections 31 set at the front and the rear end for engagement within the notches 213 of the brush head 21, an elongated slide groove 32 formed and extending axially at the top along the tooth brush in a longitudinal direction, and a plurality of positioning dowels 33 at both sides of the slide groove 32.

The head cover 4 includes a stopper 41 formed at the front, a rod-like slide rib 42 provided on the bottom surface and extending longitudinally of the brush, two pairs of positioning recesses 43 symmetrically and oppositely formed at both ends, and stepped tracks 44 respectively formed at both sides.

The tongue scaler 5 includes a tenon-like front slide guide 51 and an oval pull end 52.

The handle cover 6 includes a plurality of pairs of positioning dowels 61 symmetrically formed on the top, a longitudinal groove 62 formed on the top to define therein a slide way 63, a curved rear end 64, and a stop wall 65 formed on said curved rear end 64.

When in assembly, the rod-like slide guide 42 is set in the slide groove 32 of the bristle holder 3. The head cover 4 includes a plurality of anti-skid stripes 45 engageable by the user to push the head cover 4 forward to permit the front stopper 41 to be stopped against the side edge of brush head 21 and the positioning recesses 43 to be engaged with the positioning dowels 33. The handle cover 6 is further attached to the handle portion 22 of the brush handle 2 by engaging the positioning dowels 61 within the positioning recesses 231 of the handle portion 22 in any appropriate manner well known in the art to secure cover 6 to handle portion 2 and; allow the tongue scaler 5 to slide in the slide way 63 by means of its tenon-like slide guide 51. Through the said arrangement, the tongue scaler 5 is allowed to slide along the groove 62 between extended and retracted positions relative to the brush handle 2, with full extension being determined by engagement of guide 51 against the stop wall 65.

Referring to FIG. 3, after the projections 31 of the bristle holder 3 are respectively set in the notches 213 of the brush head 21 and the bristle holder 3 is set in the receiving trough 211 of the brush head 21, the rod-like slide rib 42 of the head cover 4 is set in the slide groove 32 of the bristle holder 3. By means of the anti-skid stripes 45, the head cover 4 is pushed ahead to let the stepped tracks 44 slide forward along the guide tracks 212, so as to permit the positioning dowels 33 of the bristle holder 3 to be respectively set in the positioning recesses 43 of the head cover 4. Thus, the head cover 4 becomes coupled with the brush head 21 to firmly retain the bristle holder therebetween. In case the bristle holder 3 is damaged and has to be replaced by a new one, the head cover 4 is pushed away from the brush head 21 in a reverse direction to disengage the positioning recesses 43 from the positioning dowels 33. When it is desired to use the tongue scaler 5, the latter extended out, by means of the oval pull handle 52, to the maximum extent until the tenon-like slide guide 51 engages the stop wall 65. After use, the tongue scaler 5 is pushed inward by the oval pull handle 52 to slide along the groove 62. As soon as the oval pull end 52 is stopped against the curved rear end 64 of the handle cover 6, the tongue scaler 5 becomes completely retracted inside the brush handle 2.

Referring to FIG. 4, when the user wishes to use the tongue scaler to remove the fur from lingual body before or after brushing of teeth, the tongue scaler 5 is pulled out by means of the oval pull handle 52, to the exent when the tenon-like slide guide 51 is stopped by the stop wall 65 of the handle cover 6. By bending the tongue scaler 5 into a curved configuration and through reciprocating motion, the tongue scaler 5 is used to scale off the fur from the tongue.

In conclusion, the present invention provides a replaceable tooth brush with tongue scaler which is convenient to detach and assemble, inexpensive to manufacture, and practical in use to efficiently clean the teeth and tongue.

I claim:

1. A toothbrush comprising:
   (a) a brush handle and an integrally formed brush head at one end of the handle, the brush head and brush handle extending along a common longitudinal axis;
   (b) the brush head including a longitudinal receiving trough formed therein, a pair of inwardly directed longitudinal guide tracks on opposite sides of the trough and a pair of longitidinally spaced notches formed in a front end and a rear end of the head;
   (c) a bristle holder for supporting a plurality of bristles, the bristle holder being detachable engageable within the receiving trough and including a pair of longitudinally spaced projections formed in a front end and a rear end of the holder, the projections being engageable within the pair of notches of the brush head, a longitudinal slide groove formed in the bristle holder and a plurality of positioning dowels extending outwardly from the bristle holder on opposite sides of the slide groove;
   (d) a head cover including a stopper formed at a front end, a slide rib extending longitudinally along a bottom surface of the cover, a plurality of positioning recesses formed on opposite sides of the ribs for engagement by the positioning dowels, and a pair of longitudinal tracks formed on opposite sides of the cover for slidable engagement within the guide tracks of the brush head;
   (e) an elongate tongue scaler including a tenon formed at one end and a handle means formed at another end thereof; and
   (f) a handle cover including a plurality of dowels for securing the handle cover to the handle so as to define a longitudinal space therebetween for slidably receiving the tongue scaler therein, the handle cover including a longitudinal groove having one end terminating in a stop wall, the tenon being slidably engageable within the longitudinal groove to permit the tongue scaler to be disposed between a retracted position within the handle and an extended position of use wherein the tenon engages the stop wall to prevent detachment of the scaler from the handle.

* * * * *